US009750511B2

(12) United States Patent
Goodfellow et al.

(10) Patent No.: US 9,750,511 B2
(45) Date of Patent: Sep. 5, 2017

(54) UNICONDYLAR KNEE REPLACEMENT (75) Inventors: John Goodfellow, Oxford (GB); Colin Hunsley, legal representative, Basingstoke (GB); John O'Conner, Oxford (GB); Chris Dodd, Oxford (GB); David Murray, Oxford (GB)

(73) Assignee: Biomet UK Limited, Bridgend South Glamorgan (GB)

( * ) Notice: Subject to any disclaimer, the term of this patent is extended or adjusted under 35 U.S.C. 154(b) by 1190 days.

(21) Appl. No.: 13/640,620

(22) PCT Filed: Apr. 20, 2011

(86) PCT No.: PCT/GB2011/050780
§ 371 (c)(1),
(2), (4) Date: Feb. 18, 2013

(87) PCT Pub. No.: WO2011/131983
PCT Pub. Date: Oct. 27, 2011

(65) Prior Publication Data
US 2013/0204258 A1 Aug. 8, 2013

(30) Foreign Application Priority Data
Apr. 20, 2010 (GB) .................................. 1006590.2

(51) Int. Cl.
*A61B 17/58* (2006.01)
*A61B 17/60* (2006.01)
(Continued)

(52) U.S. Cl.
CPC ........ *A61B 17/1717* (2013.01); *A61B 17/155* (2013.01); *A61B 17/157* (2013.01);
(Continued)

(58) Field of Classification Search
CPC ..... A61B 17/15; A61B 17/154; A61B 17/155; A61B 17/157; A61B 17/158;
(Continued)

(56) References Cited

U.S. PATENT DOCUMENTS 4,703,751 A * 11/1987 Pohl ................................ 606/62
5,234,433 A 8/1993 Bert et al.
(Continued)

FOREIGN PATENT DOCUMENTS

EP 0709061 A1 5/1996
EP 1862149 A2 12/2007
(Continued)

OTHER PUBLICATIONS

FR002664157A1 document and translation attached.*
(Continued)

*Primary Examiner* — Kevin T Truong
*Assistant Examiner* — Si Ming Ku
(74) *Attorney, Agent, or Firm* — Schwegman Lundberg & Woessner, P.A.

(57) ABSTRACT

A kit of parts for use in unicondylar knee replacement of a patient having a femur and a tibia comprises a drill guide and an intramedullary rod, the intramedullary rod being sized to fit within the intramedullary canal of the femur of the patient. The drill guide is arranged so as to engage a distal end of the intramedullary rod to that which engages the patient's intramedullary canal, and is formed with a foot portion sized to fit between the patient's femur and tibia before any bone is removed from the femur or tibia. The drill guide provides a guide for drilling of at least one hole in the femur. A further kit of parts for use in unicondylar knee replacement of a patient having a femur and a tibia comprises a femoral component for implantation in the femur, the femoral component having a bearing surface having a
(Continued)

radius of curvature, and a guide spoon. The guide spoon has a bowl-shaped portion with an internal radius of curvature the same as that of the bearing surface, and a handle portion extending from the bowl-shaped portion. Methods of performing unicondylar knee replacement are also described.

15 Claims, 5 Drawing Sheets

(51) Int. Cl.
| | |
|---|---|
| *A61F 2/00* | (2006.01) |
| *A61B 17/17* | (2006.01) |
| *A61B 17/15* | (2006.01) |
| *A61F 2/38* | (2006.01) |
| *A61B 17/72* | (2006.01) |
| *A61F 2/46* | (2006.01) |

(52) U.S. Cl.
CPC ........ *A61B 17/1764* (2013.01); *A61F 2/3868* (2013.01); *A61B 17/72* (2013.01); *A61F 2/4684* (2013.01); *A61F 2002/3895* (2013.01)

(58) Field of Classification Search
CPC . A61B 17/1764; A61B 17/1717; A61B 17/72; A61B 17/1675; A61B 17/14; A61B 17/141; A61F 2/4684
USPC ........ 606/87–90, 96; 623/13.12, 20.14, 20.3, 623/20.31
See application file for complete search history.

(56) References Cited

U.S. PATENT DOCUMENTS

| | | | |
|---|---|---|---|
| 5,282,803 A | 2/1994 | Lackey | |
| 5,314,482 A * | 5/1994 | Goodfellow | A61B 17/1637 606/88 |
| 5,447,515 A * | 9/1995 | Robicsek | A61B 17/11 606/158 |
| 5,911,723 A | 6/1999 | Ashby et al. | |
| 7,172,597 B2 * | 2/2007 | Sanford | A61B 17/155 606/88 |
| 7,306,607 B2 | 12/2007 | Metzger | |
| 2002/0029038 A1 | 3/2002 | Haines | |
| 2003/0100906 A1* | 5/2003 | Rosa | A61B 17/155 606/86 R |
| 2004/0167531 A1 | 8/2004 | Hodorek | |
| 2005/0055028 A1 | 3/2005 | Haines | |
| 2009/0222014 A1* | 9/2009 | Bojarski | A61B 17/155 606/88 |
| 2009/0264890 A1 | 10/2009 | Duggineni et al. | |
| 2011/0213375 A1* | 9/2011 | Sikora | A61B 17/157 606/87 |
| 2012/0209275 A1* | 8/2012 | Fox | A61B 17/157 606/88 |

FOREIGN PATENT DOCUMENTS

| | | | |
|---|---|---|---|
| FR | 2664157 A1 * | 1/1992 | .......... A61B 17/155 |
| FR | 2672488 A1 | 8/1992 | |
| GB | 2426198 A | 11/2006 | |
| GB | 2472622 A | 2/2011 | |
| JP | H 10137273 A | 5/1998 | |
| JP | 2005046625 A | 2/2005 | |
| WO | WO 2004/016204 A1 | 2/2004 | |
| WO | WO-2011131983 A2 | 10/2011 | |
| WO | WO-2011131983 A3 | 10/2011 | |

OTHER PUBLICATIONS

Notification of Transmittal of the International Search Report and the Written Opinion of the International Searching Authority dated Oct. 18, 2011 in connection with International Patent Application No. PCT/GB2011/050780.
UK Search Report of the UK IPO Searching Authority dated Aug. 3, 2010 in connection with GB Patent Application No. GB1006590. 2, 3 pages.
UK Search Report of the UK IPO Searching Authority dated May 4, 2011 in connection with GB Patent Application No. GB1006590. 2, 3 pages.
Translation of Notice of Reason(s) for Rejection dated Dec. 9, 2014 in connection with Japanese Application No. 2013-5055144; 3 pages.
"European Application Serial No. 11730049.1, Communication Pursuant to Article 94(3) EPC mailed Mar. 16, 2015", 5 pgs.
"European Application Serial No. 11730049.1, Communication Pursuant to Article 94(3) EPC mailed Aug. 20, 2014", 5 pgs.
"European Application Serial No. 11730049.1, Communication pursuant to Rules 161(1) and 162 EPC mailed Dec, 5, 2012", 2 pgs.
"European Application Serial No. 11730049.1, Response filed Feb. 19, 2015 to Communication Pursuant to Article 94(3) EPC mailed Aug. 20, 2014", 6 pgs.
"European Application Serial No. 11730049.1, Response filed Jun. 12, 2013 to Communication pursuant to Rules 161(1) and 162 EPC mailed Dec. 5, 2012", 15 pgs.
"European Application Serial No. 11730049.1, Response filed Sep. 18, 2015 to Communication Pursuant to Article 94(3) EPC mailed Mar. 16, 2015", 2 pgs.
"International Application Serial No. PCT/GB2011/050780, International Preliminary Report on Patentability mailed Nov. 1, 2012", 11 pgs.
"Israel Application Serial No. 222106, Office Action mailed May 12, 2015", (W/ English Translation), 6 pgs.
"Japanese Application Serial No. 2013505544, Office Action mailed Nov. 10, 2015", (W/ English Translation), 3 pgs.
"Japanese Application Serial No. 2013505544, Response filed Jan. 20, 2016 to Office Action mailed Nov. 10, 2015", (W/ English Translation), 9 pgs.
"Japanese Application Serial No. 2013505544, Response filed Jun. 8, 2015 to Office Action mailed Dec. 9, 2014", (W/ English Translation), 3 pgs.
"Japanese Application Serial No. 2013505544, Voluntary Amendment filedApr. 8, 2014", (W/ English Translation), 10 pgs.

* cited by examiner

Fig. 12

UNICONDYLAR KNEE REPLACEMENT

CROSS-REFERENCE TO RELATED APPLICATION(S)

The present application claims priority under 35 U.S.C. §365 to International Patent Application No. PCT/GB2011/050780 filed Apr. 20, 2011. International Patent Application No. PCT/GB2011/050780 claims priority under 35 U.S.C. §365 and/or 35 U.S.C. §119(a) to United Kingdom Patent Application No. 1006590.2 filed Apr. 20, 2010 and which are incorporated herein by reference into the present disclosure as if fully set forth herein.

TECHNICAL FIELD

The present invention relates to kits of parts for, and methods of, performing unicondylar knee replacement.

BACKGROUND

The knee comprises three inter-dependent joints in three separate compartments, all surrounded by a fibrous capsule covered by the skin. The medial tibio-femoral joint involves contact between the thigh bone (the femur) and the leg bone (the tibia) on the inside of the lower limb. The lateral tibio-femoral joint involves contact between the femur and the tibia on the outside of the lower limb. The patello-femoral joint involves contact between the femur and the knee cap (the patella) on the front of the lower limb.

The front of the lower (distal) end of the femur comprises a flanged concave groove providing a track for the patella. The back of the distal femur divides into two separate near-spherical concave condyles making contact with the tibia. The upper surface of the tibia is like a plateau which is slightly dished on the medial side for contact with the medial femoral condyle forming the medial tibio-femoral joint and slightly convex on the lateral side for contact with the lateral femoral condyle forming the lateral tibio-femoral joint with a protrusion (the tibial eminence) running from front to back between the joints.

The articulating surfaces in each joint are covered with thin layers of a tough protective layer called cartilage, and are lubricated by synovial fluid secreted from a membrane on the inner surface of the fibrous capsule surrounding the knee. The surfaces of the tibio-femoral joints are further separated by the menisci, semi-circular semi-lunar collagen bundles oriented circumferentially. Each bundle is securely attached at each end to the tibia. The menisci form closely-fitting sockets for the femoral condyles bringing the dissimilar surfaces of the femur and tibia into closer conformity.

The bones are held together actively by muscles with their tendons which span the joints and passively by ligaments and the joint capsule. The ligaments comprise bundles of collagen fibres running mainly longitudinally. The collateral ligaments arise on the external surfaces of the medial and lateral condyles. The medial collateral ligament inserts into the external medial surface of the proximal tibia. The lateral collateral ligament inserts into the proximal surface of the fibula. The medial collateral ligament is a much larger and stiffer structure than the lateral collateral ligament. The cruciate ligaments arise from the internal surfaces of the femoral condyles and insert into the tibial eminence.

The ligaments and the bones together form a mechanism which controls a complex pattern of movement of the bones on each other. In the unloaded state, flexion of the knee to 130° about a transverse axis is accompanied by approximately 25° rotation about the axis of the tibia (axial rotation) and approximately 5° about an anteroposterior axis (abduction-adduction). These movements are accommodated by mainly antero-posterior translations of the tibio-femoral contact areas so that the bones roll as well as slide on each other and the patella slides over the anterior femur.

Under load, the ligaments stretch and the articular surfaces indent, significantly modifying the relationship between flexion, axial rotation and abduction-adduction and between flexion and contact area translations. Movements at the knee are therefore load and activity dependent.

Damage to the articular surfaces or to the ligaments changes the patterns of movement of the bones on each other and response of the joint to load. Osteoarthritis follows from failure of the cartilage in one or other of the three joints, leading to bone-on-bone contact and the onset of pain. Frequently, osteoarthritis first manifests itself in the medial compartment, while the ligaments remain intact. The disease can remain confined to the medial compartment until the anterior cruciate ligament fails and the disease then spreads to the other two compartments. No drug treatment has been found which reverses these processes.

Total knee replacement is the most common surgical treatment for osteoarthritis, involving replacement of the articular surfaces of all three compartments and sacrifice of some of the ligaments. Partial knee replacement involves replacement of the articular surfaces in only one compartment, leaving intact the surfaces of the other two compartments and all of the ligaments. Partial knee replacement can act prophylactically, reducing the rate of development of the disease in the other compartments. Partial knee replacement is surgically more demanding and is not always used when it is indicated.

To implant the prosthetic components of a knee replacement, sufficient sections of bone first have to be removed from the surfaces of the tibia and the femur. The tibial surface is sawn first, using a saw guide that is applied with its shaft parallel to the long axis of the tibia and its upper end nailed to the exposed bone. The level of the guide is estimated, usually consarvatively so that more bone can be resected if required.

Once the initial resection of the tibia has taken place, the femur is prepared for the implantation of the femoral component of the knee replacement. Holes are drilled for insertion of the femoral saw block, the spigots for milling and the trial femoral component. The positions and angles of these holes are referenced by inspection off features of the femur, and the position of the resected tibial plateau is checked and revised if necessary. Once the initial cutting, milling and trimming of the femur has taken place, a trial femoral component and a tibial template are inserted. The new gap between the femoral and tibial components is measured at the extremes of knee flexion, and the femur is further milled to equalise these flexion gaps. Final trimmings of the femur and tibia take place before the appropriate bearing is fitted and the final components are cemented in place.

SUMMARY

According to a first aspect of the invention, there is provided a kit of parts for use in unicondylar knee replacement of a patient having a femur and a tibia, comprising a drill guide and an intramedullary rod, the intramedullary rod being sized to fit within the intramedullary canal of the femur of the patient, the drill guide being arranged so as to engage a distal end of the intramedullary rod to that which engages the patient's intramedullary canal, the drill guide being formed with a foot portion sized to fit between the patient's femur and tibia before any bone is removed from the femur or tibia, the drill guide providing a guide for drilling of at least one hole in the femur.

Thus, the drill guide has two points of reference on the patient's femur; firstly, the intramedullary rod, and, secondly, the foot portion being fitted between the unresected tibia and femur. Thus, the drill guide can be held securely and accurately in place, to ensure accurate and consistent drilling.

In order to fit between the unresected tibial and femoral components, the foot portion may have a maximum thickness of 2 mm.

Typically, the guide will comprise at least one hole, through which a drill bit can be passed in order to drill the or each hole in the femur. Typically, there will be a main hole, such as may be used to drill a hole for a main peg on the femoral component to be implanted. The distance between the centre of the main hole and the foot portion may be equal to a radius of the femoral condyle. The distance between the centre of the main hole and the foot portion may also be equal to a radius of the femoral component.

The guide may comprise a further hole for drilling a further hole in the femur; the distance between the main hole and the further hole in the drill guide may be equal to a distance between the main peg and a further peg in the femoral component to be implanted. The distance between the main hole and the further hole in the drill guide may also be equal to a distance between two holes in a saw guide used in a resection of the femur.

The drill guide may connect to the intramedullary rod by means of a linkage. The linkage may comprise at least one rod which engages the end of the intramedullary rod. The linkage may also comprise at least one rod which engages at least one hole in the drill guide. The holes in the drill guide may be positioned such that, for a left knee the linkage engages a first hole and not a second hole, and for a right knee the linkage engages a second hole and not the first hole. Thus, the same apparatus can be used for right or left knees.

The kit of parts may further comprise at least one femoral component. At least one femoral component may be a trial femoral component which is temporarily implanted in the femur. At least one femoral component may be a prosthetic femoral component which is permanently implanted in the femur. At least one prosthetic femoral component may have a radius equal to that of at least one trial femoral component.

According to a second aspect of the invention, there is provided a kit of parts for use in unicondylar knee replacement of a patient having a femur and a tibia, comprising a femoral component for implantation in the femur, the femoral component having a bearing surface having a radius of curvature, and a guide spoon, the guide spoon having a bowl-shaped portion with an internal radius of curvature the same as that of the bearing surface, and a handle portion extending from the bowl-shaped portion.

This spoon guide can therefore provide an accurate reference point for further resection of the patient's knee, typically the tibia. Typically, the femoral component will be a trial femoral component, which is only temporarily implanted in the femur.

The bowl-shaped portion will typically, have a rim; the rim and the handle portion may be co-planar in a common plane. The kit of parts may further comprise a clamp and a horizontal saw guide, the clamp being arranged to clamp to the hand portion and to space the saw guide from the handle portion by a pre-determined distance, typically in the direction perpendicular to the common plane. Thus, the "horizontal" cut in the tibia can be correctly placed.

The kit of parts may further comprise a vertical saw guide, which comprises a first arm which engages a hole in the femoral component, the hole being keyed such that the first arm will not rotate in the hole, and a second arm which extends at an angle from the mechanical axis of the femur. Typically, the angle will be approximately 7 degrees, such that the second arm runs parallel to the diaphyseal femoral axis.

The hole may have rotational symmetry (typically of even order) such that the first arm can be placed in at least two positions therein to work with left and right knees. Typically, the hole will be square or rectangular in cross section.

In order to enable the correct cut to be made by placing a saw against the vertical saw guide and the rim of the spoon, the rim of the spoon may be circular with a radius sized so that, when a wall of the tibial component is installed in the cut that is to be made, there is a gap of predetermined size—typically approximately 1 mm—between the wall and a bearing, typically a meniscal bearing, to be inserted between the tibial and femoral components. Typically, the radius will be the sum of half the width of the bearing, the width of the wall and the distance between the bearing and the wall, less the width of the saw blade to be used. The kit of parts may further comprise at least one of the tibial component and the saw blade.

The first and second arms of the vertical saw guide may be offset by the radius of the rim also.

The kit of parts may further comprise a U-shaped channel for connecting to the second arm of the vertical saw guide and arranged to constrain a saw blade placed therein to cut parallel to the second arm.

The dimensions of the vertical saw guide may be made so that the slot mechanism points both at the correct angle and in the correct position for the cut. The length x of the crank portion may be calculated as:

$$x = r/\cos\theta - y\tan\theta$$

where $\theta$ is the angle at which the guide portion is axially bent away from the axis of the first, end, y is the radial distance of the crank portion away from the centre of the spoon, and r is the radius of the rim of the spoon According to a third aspect of the invention, there is provided a method of performing unicondylar knee replacement of knee of a patient, comprising using the kit of parts of the first aspect of the invention by placing the intramedullary rod in the intramedullary canal of the femur of the knee, connecting the drill guide to the intramedullary rod, placing the foot portion between the femur and the tibia of the knee, aligning the drill guide laterally to the central prominence of the femoral condyle and then drilling a hole in the femur guided by the guide.

Thus, the drill guide has two points of reference on the patient's femur; firstly, the intramedullary rod, and, secondly, the central prominence of the femoral condyle. This ensures accurate and consistent drilling. A rotational degree of freedom may allow the foot portion to move around the spherical surface of the condylar cartilage. Typically, it will be the main hole of the drill guide that is aligned laterally with the central prominence of the femoral condyle.

The method may comprise drilling a first hole in the femur by passing a drill bit through the main hole and then drilling with the bit. The method may comprise leaving the drill bit in place after the first hole has been drilled, and then rotating the drill guide about the main hole (typically having disconnected the drill guide from the intramedullary rod after the first hole has been drilled) to correctly position the further hole, then drilling a second hole in the femur through the further hole in the drill guide.

The method may comprise the implantation of a femoral component, typically a trial femoral component that is only implanted temporarily. Typically, once the first hole and any second hole have been drilled, the femoral condyle to be replaced can be milled and cut, typically using prior art techniques, and the femoral component implanted using the first and/or second holes as positional guides.

According to a fourth aspect of the invention, there is provided a method of performing unicondylar knee replacement of a knee of a patient using the kit of parts of the second aspect of the invention, comprising implanting the femoral component in the femur of the knee, inserting the spoon with its bowl against the bearing surface.

This spoon guide can therefore provide an accurate reference point for further resection of the patient's knee, typically the tibia. The femoral component may be a trial femoral component that is only implanted temporarily.

The method may further comprise the step of clamping the clamp and the horizontal saw guide to the handle portion; typically this will space the saw guide from the handle portion by a pre-determined distance, typically in the direction perpendicular to the common plane. The method may then comprise cutting the tibia along a plane indicated by the horizontal saw guide. Thus, the "horizontal" cut in the tibia can be correctly placed.

The method may further comprise the step of inserting the vertical saw guide into the femoral component, then sawing into the tibia guided by the vertical saw guide. Thus, the "vertical" cut can be achieved. Typically, the vertical cut will be extended to meet the horizontal cut.

According to a fifth aspect of the invention, there is provided a method of performing unicondylar knee replacement of a patient, comprising implanting a femoral component in the femur of a knee of the patent before a tibial component is implanted in the tibia of the knee. In the preferred embodiment, the femoral component once implanted is used to determine the correct position for resectioning of the tibia in advance of the implantation of the tibial component.

The femoral component may be a trial femoral component that is only implanted temporarily.

Typically, the method will comprise the steps of a method according to the third aspect of the invention, followed by a method according to the fourth aspect of the invention.

BRIEF DESCRIPTION OF THE DRAWINGS

There now follows, by way of example only, an embodiment of the invention, described with reference to, and as illustrated in, the accompanying drawings, in which.

DETAILED DESCRIPTION

FIGS. 1 to 4 show a kit of parts according to a first embodiment of the invention being used to effect the initial stages of a unicondylar knee replacement. In this first stage, a femoral component 3 (FIG. 5) is to be fitted into the femur 1 of a patient, and so the femur must be resected to allow for the implantation.

Figure 1:
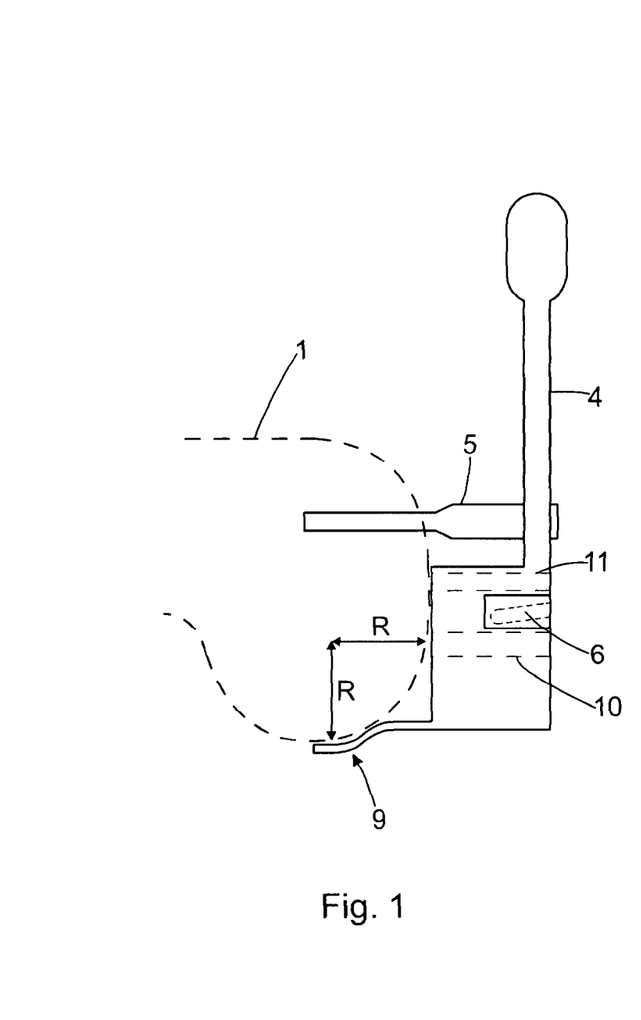
FIG. 1 shows a side elevation of a kit of parts according to a first embodiment of the invention being used to implant a femoral component.
Figures 2, 3:
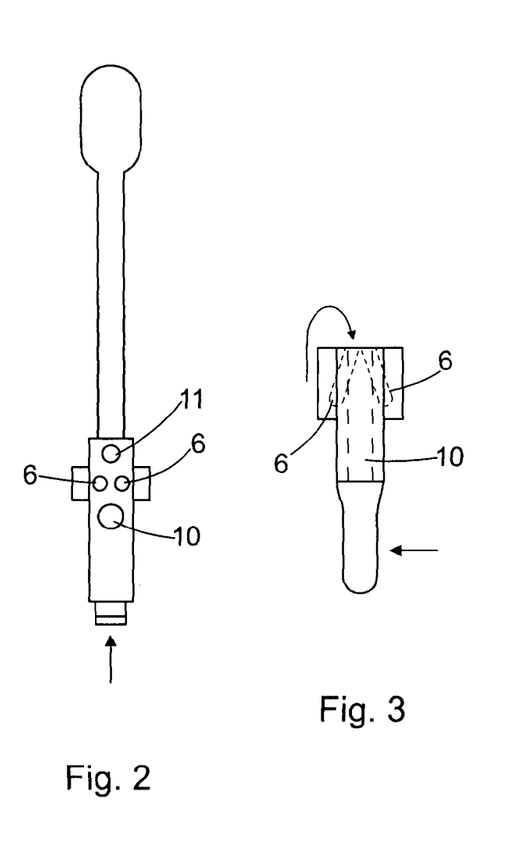
FIG. 2 shows a further side elevation of the drill guide of the kit of parts of FIG. 1.
FIG. 3 shows an underside plan view of the drill guide of FIG. 2.

In order to do so, a drill guide 4 is used to determine the position of the two holes that are required in the femur to support the locating peg or pegs of the femoral component 1. This is used in conjunction with an intramedullary rod 5, which is inserted into the intramedullary canal of the femur 1 in order to provide a fixed location. A narrow foot portion 9, having a thickness of about 2 mm is provided at a lower end of the drill guide 4; the foot portion 9 can fit between the patient's femur and tibia before any resection takes place.

Figure 4:
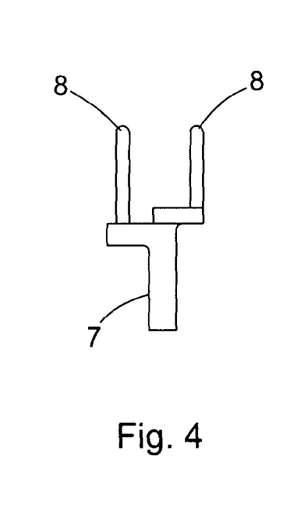
FIG. 4 shows the linkage used to connect the intramedullary rod and drill guide of the kit of parts of FIG. 1.

In order to provide the location of the first hole to be drilled, two holes 6 are provided in the drill guide to accept one of two rods 8 comprised in a linkage 7. The holes 6 extend into the drill guide at an angle of 10 degrees to the horizontal towards the foot portion 9 and at an angle of 7 degrees horizontally towards either side of a vertical drill hole 10, which will be discussed in more detail below. Only one hole 6 will be used for a given knee, as the combination allows the use of this kit of parts for both left and right knees. The intramedullary rod 5 is adapted to accept the other one of the two rods 8 which is not inserted into a hole 6, thus linking the drill guide with the intramedullary rod and maintaining a predefined spacing and alignment between them. Linking the drill guide to the intramedullary rod in this way ensures that the drill hole is directed at an angle of 10 degrees to the horizontal away from the foot portion 9 and at an angle of 7 degrees horizontally, parallel to the horizontal component of the diaphyseal femoral axis.

The drill hole 10 provides the surgeon with a guide as to where to drill the main drill hole for the main peg of the femoral component. The distance between the drill hole and the foot portion 9 is the same as the radius of curvature R of the femoral component 1.

A further drill hole 11 is provided, which will provide the surgeon with the location for a further, smaller, peg hole as described below.

Once the drill guide 4 and the intramedullary rod 5 are linked, the position of the drill guide 4 is adjusted so that the drill hole 10 is aligned with the centre of the correct condyle. A drill is then used to drill the main peg hole. The drill bit is left in place in the hole, whilst the linkage 7 is removed. The drill guide 4 is then rotated about the drill hole 10, until the further drill hole 11 is aligned centrally along the prominence of the femoral condyle, below the first hole, thus ensuring that the distance between the two holes is correct. The smaller hole can then be drilled through the further drill hole 11. Once that is done, the drill guide 4 and drills are removed, and the primary milling and cutting of the condyle 1a carried out using existing methods. The trial, temporary, femoral component 3 is then inserted.

As will be explained below, now that the trial femoral component 3 has been implanted, this can be used to provide a reference for the correct position in which the cuts to the patient's tibia should be made. This makes for an overall more accurate set of cuts, and may reduce the need for repeated cuts and corrections mid-surgery.

Figures 5, 6, 7:
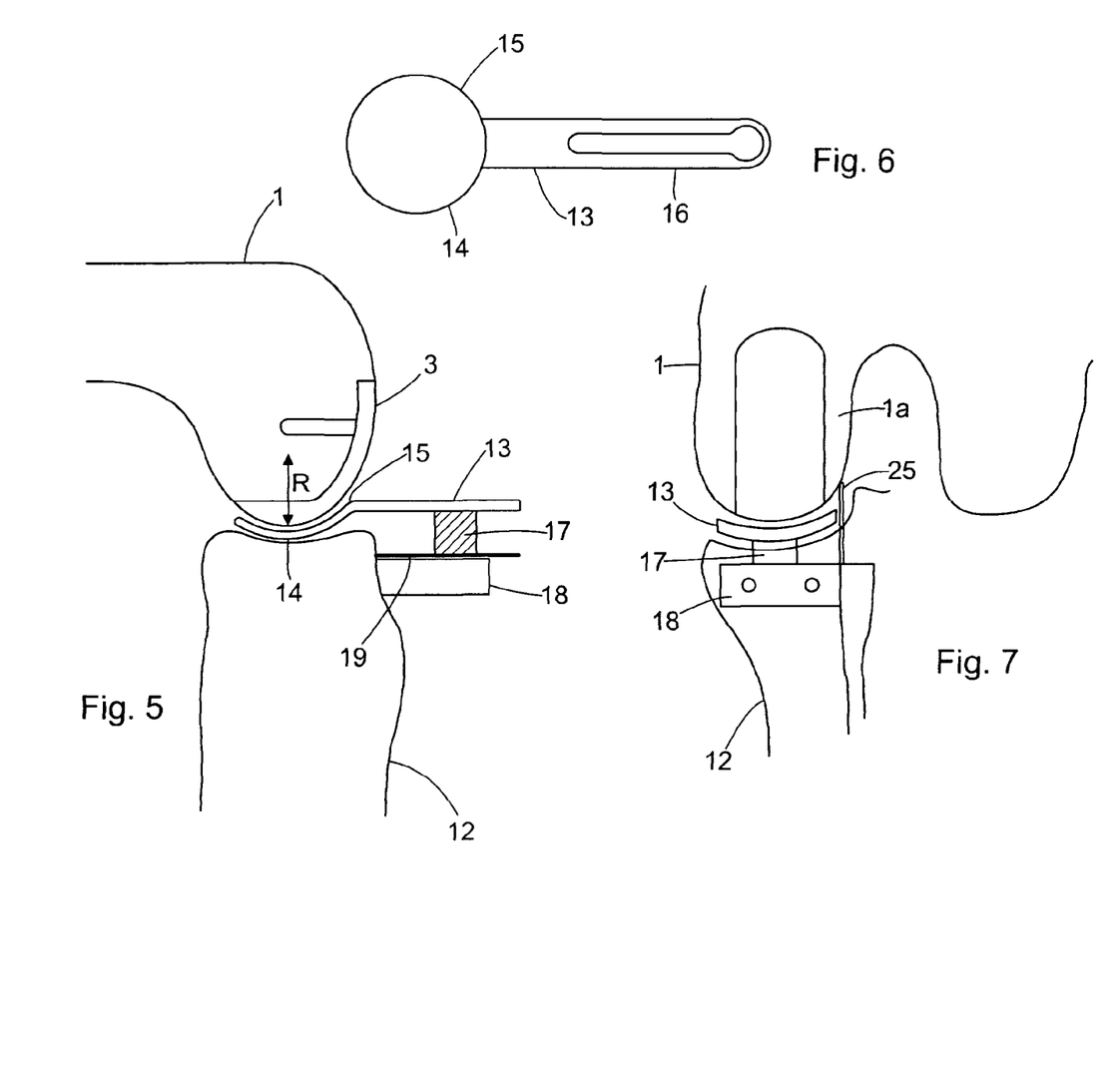
FIG. 5 shows further elements of the kit of parts of FIG. 1, used to implant a tibial component.
FIG. 6 shows a plan view of a spoon being part of the kit of parts of FIG. 5.
FIG. 7 shows a "horizontal" cut being made in the tibia, using the kit of parts of FIG. 5.

In the next stage, shown in FIGS. 5 to 7 of the accompanying drawings, the first, horizontal cut is made to the patient's tibia 12. A guide spoon 13 is used, which has a bowl portion 14 having an inner radius of curvature the same as the radius of curvature R of the femoral component 3. The bowl portion 14 has a rim 15 and a handle portion 16 extending from and co-planar with the rim 15. It has a thickness of 1 mm.

The guide spoon 13 is inserted, with the bowl portion 14 under the trial femoral component 3 and clamped using the handle portion and a clamp 17 to a horizontal saw guide 18, which guides the surgeon to the correct location for the horizontal cut. The clamp ensures that the spoon handle 16 is parallel to the horizontal saw guide 18 and that the cut 19 is the desired distance—7.5 mm—below the femoral component, allowing for the thickness of the platform of the tibial template and the meniscal bearing insert (3.5 mm and 4.5 mm respectively).

Figure 8:
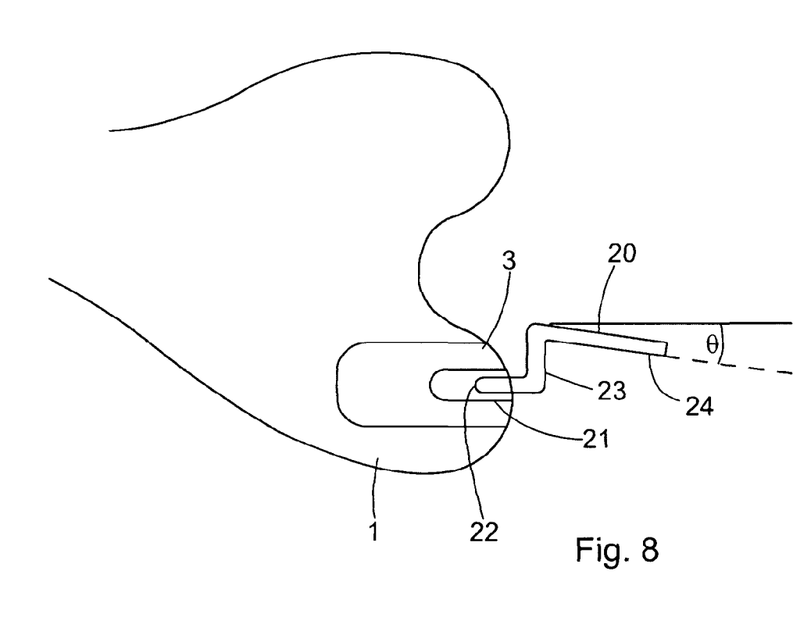
FIG. 8 shows a side elevation of the vertical saw guide of the kit of parts of FIG. 5 fitted to the femoral component.
Figure 9:
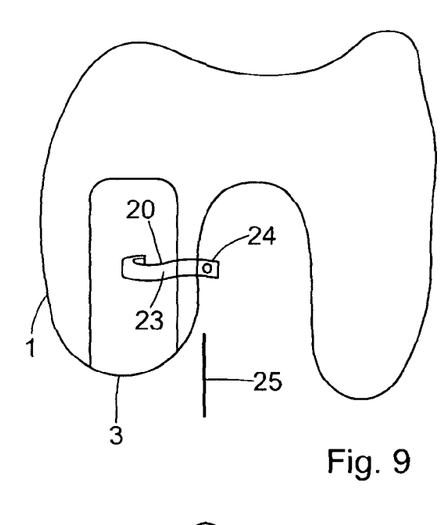
FIG. 9 shows a plan view of the vertical saw guide of FIG. 8 being used to make a "vertical" cut in the tibia.
Figure 10:
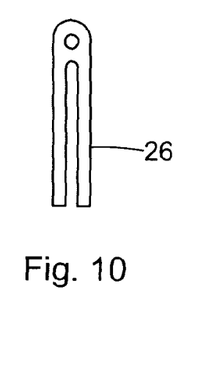
FIG. 10 shows an optional saw guide that can be used with the vertical saw guide of FIG. 8.

Once the horizontal cut is made, the procedure can proceed to the situation shown in FIGS. 8 to 10 of the accompanying drawings. A vertical saw guide 20 is used, which comprises a generally elongate body of square cross section, a first end 22 of which is received in a square hole 21 in the femoral component 3. Being square, the vertical saw guide 20 can be received in the hole 21 in two orientations to allow for left or right knees to be operated upon (of course, there will be two further orientations in which such insertion is possible, but these are not in practice used).

The hole 21 in the femoral component is vertically in line with the peg of the trial femoral component. The axis of this peg is parallel with the plane of the flat portion of the component (i.e. horizontal) so the axis of the hole is on the same line as that of the peg. The hole will be central in the femoral component 3, given that it will be used in both left and right knees.

The vertical saw guide 20 then comprises a crank portion 23 connected to a guide portion 24 at the end distal from the first end 22. The crank portion 23 axially separates the first end 22 from the guide portion 24. The guide portion is also axially bent away from the axis of the first end and of the mechanical axis of the femur by an angle θ of 7 horizontal degrees, so as to be aligned with the diaphyseal femoral axis.

Figure 11:
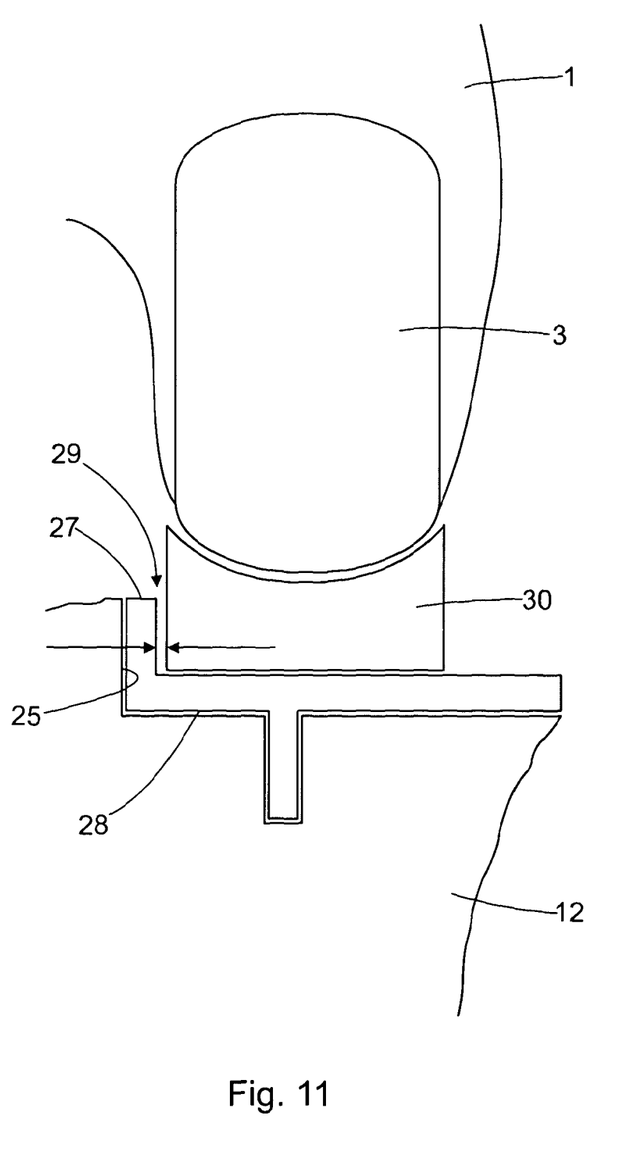
FIG. 11 shows the horizontal positioning of the meniscal bearing in relation to the tibial component.

The saw for the vertical tibial cut 25 is positioned parallel to the guide portion 24 and against the rim 15 of the spoon 13. As shown in FIG. 11, the dimensions of the rim 15 ensure that, when the wall 27 of the tibial component 28 is flush against the vertical tibial cut 25, there is a 1 mm gap 29 between the wall 27 and the bearing 30.

Accordingly, the rim 15 of the spoon 13 is circular with a radius equal to: ½ (bearing insert width)+width of wall+distance between bearing and wall−width of saw blade. Apart from the bearing insert width, these values are respectively 1.5 mm, 1 mm and 1 mm. The crank portion 23 is also of this length.

Figure 12:
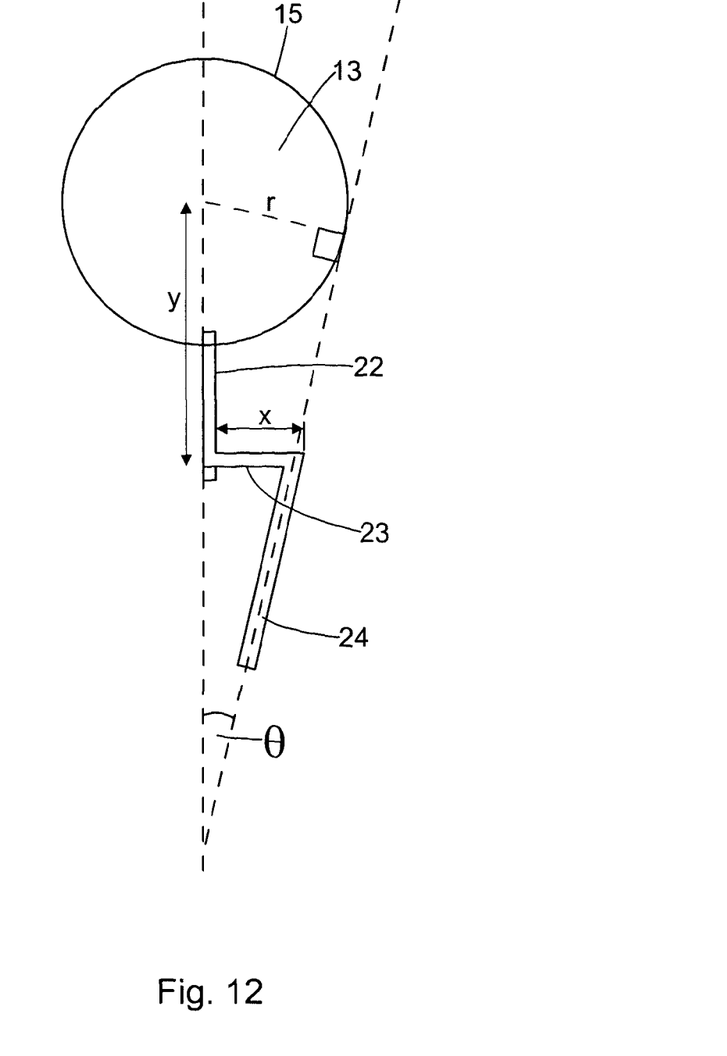
FIG. 12 shows the dimensions of the vertical saw guide.

A slot mechanism 26 (shown in FIG. 10) may be fitted on the guide portion 24. It is of the form of a U-shaped slot, and will correctly orient the saw blade. The dimensions of the vertical saw guide 20 can be made so that the slot mechanism 26 points both at the correct angle and in the correct position for the cut. The length x of the crank portion 23 can be given as:

$$x = r/\cos\theta - y\tan\theta$$

where
 θ is the angle at which the guide portion 24 is axially bent away from the axis of the first end 22,
 y is the radial distance of the crank portion 23 away from the centre of the spoon 13, and
 r is the radius of the rim 15 of the spoon 13; these dimensions are shown in more detail in FIG. 12 of the accompanying drawings.

Once these cuts have been made, the tibial plate is fitted using existing methods which may be with cement or cementless. With the tibial platform in place, the surgeon finishes the operation by fitting the implantable femur and selecting the appropriate bearing to balance the ligaments in extension and flexion using existing practices.

The invention claimed is:

1. A system of parts for use in unicondylar knee replacement of a patient having a femur and a tibia, comprising a drill guide and an intramedullary rod, the intramedullary rod being sized to fit within the intramedullary canal of the femur of the patient, the drill guide configured to engage a distal end of the intramedullary rod to that which is configured to engage the patient's intramedullary canal, the drill guide being formed with a foot portion sized to fit between the patient's femur and the patient's tibia before any bone is removed from the femur or the tibia, the drill guide providing a guide for drilling of at least one hole in the femur at a condyle laterally offset from the intramedullary rod;
 wherein the drill guide connects to the intramedullary rod by means of a linkage comprising at least one rod which couples to an end of the intramedullary rod, and an additional rod which couples to at least two holes in the drill guide, in which the at least two holes in the drill guide are positioned such that, for a left knee the linkage engages a first hole and not a second hole, and for a right knee the linkage engages the second hole and not the first hole.

2. The system of claim 1, in which the drill guide comprises at least one hole, through which a drill bit can be passed in order to drill the at least one hole in the femur, the at least one hole in the drill guide including a main hole, a distance between the main hole and the foot portion being equal to a radius of a femoral component to be implanted.

3. The system of claim 2, in which the guide comprises a further hole for drilling a further hole in the femur;
 a distance between the main hole and the further hole in the drill guide may be equal to a distance between a main peg and a further peg in the femoral component to be implanted.

4. The system of claim 1, comprising at least one femoral component, which is to be implanted in the femur, typically including a trial femoral component which is to be temporarily implanted in the femur and a prosthetic femoral component which is to be permanently implanted in the femur.

5. The system of claim 1, wherein the foot portion is curved to fit along a posterior portion of the condyle and has a thickness of about 2 mm.

6. The system of claim 1, wherein the at least two holes extend into the drill guide at an angle of 10 degrees to horizontal towards the foot portion, and at an angle of 7 degrees horizontal towards either side of the guide, respectively.

7. A system of parts for use in unicondylar knee replacement of a patient having a femur and a tibia, comprising:
 a drill guide and an intramedullary rod, the intramedullary rod being sized to fit within the intramedullary canal of the femur of the patient, the drill guide being configured to engage a distal end of the intramedullary rod to that which is configured to engage the patient's intramedullary canal, the drill guide being formed with a foot portion sized to fit between the patient's femur and tibia before any bone is removed from the femur or tibia, the drill guide providing a guide for drilling of at least one hole in the femur laterally offset from the intramedullary rod, and
 a linkage for connecting the drill guide to the intramedullary rod, the linkage comprising at least one rod which couples to an end of the intramedullary rod, and an additional rod which couples to at least two holes in the drill guide;
 wherein at least two holes in the drill guide are positioned such that, for a left knee the linkage engages a first hole and not a second hole, and for a right knee the linkage engages the second hole and not the first hole;
 and further comprising:
 a femoral component for implantation in the femur, the femoral component having a bearing surface having a radius of curvature, and a guide spoon, the guide spoon having a bowl-shaped portion with an internal radius of curvature same as that of the bearing surface, and a handle portion extending from the bowl-shaped portion.

8. The system of claim 7, wherein:
 the at least two holes in the drill guide are oblique to an axis of the guide for drilling of at least one hole in the femur; and
 the at least one rod and the additional rod extend from the linkage along axes that are parallel.

9. A unicondylar knee replacement system comprising:
 a drill guide comprising:
  a body configured to engage a distal end of a femur;
  a foot portion extending from the body and configured to engage a posterior portion of the femur;
  a first drill hole extending through the body and configured as a guide for drilling a hole into a distal end of a condyle of the femur along a first axis;
  a first rod hole extending into the body and diverging to a first side of the body at a first angle relative to the first axis; and
  a second rod hole extending into the body and diverging to a second side of the body at a second angle relative to the first axis; and
 a linkage for connecting to the drill guide comprising:
  a linkage body;
  a first rod extending from the linkage body along a second axis; and
  a second rod extending from the linkage body parallel to the second axis.

10. The unicondylar knee replacement system of claim 9, further comprising:
 an intramedullary rod that can receive one of the first and second rods to connect to the drill guide by the linkage;
 wherein the first rod hole and the second rod hole are positioned such that, when the intramedullary rod is engaged with the linkage, for a left knee the linkage engages the first rod hole and not the second rod hole, and for a right knee the linkage engages the second rod hole and not the first rod hole.

11. The unicondylar knee replacement system of claim 9, wherein:
 the first rod hole and the second rod hole extend into the body of the drill guide at an angle of 10 degrees to horizontal towards the foot portion;
 the first rod hole extends into the body of the drill guide at an angle of 7 degrees horizontal towards the first side of the body; and
 the second rod hole extends into the body of the drill guide at an angle of 7 degrees horizontal towards the second side of the body.

12. The unicondylar knee replacement system of claim 11, wherein the first rod hole and the second rod hole are coplanar.

13. The unicondylar knee replacement system of claim 9, wherein the drill guide further comprises a second drill hole extending through the body parallel to and spaced from the first drill hole.

14. The unicondylar knee replacement system of claim 9, wherein the foot portion has a thickness of approximately 2 mm.

15. The unicondylar knee replacement system of claim 9, wherein the body comprises:
 a bone-contacting surface configured to engage the distal end of the femur; and
 a guide surface opposite the bone-contacting surface and into which the first drill hole, the first rod hole and the second rod hole extend;
 wherein the first side surface and the second side surface are positioned between the bone-contacting surface and the guide surface.

* * * * *